(12) United States Patent
Joedicke (10) Patent No.: US 6,214,466 B1
(45) Date of Patent: Apr. 10, 2001

(54) ALGAE-RESISTANT ROOFING GRANULES

(75) Inventor: Ingo B. Joedicke, Hedgesville, WV (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 09/362,797

(22) Filed: Jul. 28, 1999

(51) Int. Cl.[7] .............................. B32B 5/16; B32B 11/00; B32B 31/00; B05D 7/00
(52) U.S. Cl. .................. 428/404; 106/15.05; 106/18.36; 427/214; 427/215; 427/219; 428/403; 428/489
(58) Field of Search .................. 106/15.05, 18.36; 427/214, 215, 219; 428/403, 404, 489

(56) References Cited

U.S. PATENT DOCUMENTS

| | | | |
|---|---|---|---|
| 3,494,727 | 2/1970 | Rapaport | 21/61 |
| 3,507,676 | 4/1970 | McMahon | 117/27 |
| 3,528,842 | 9/1970 | Skadulis | 117/27 |
| 3,560,196 | 2/1971 | Horai et al. | 71/115 |
| 3,598,627 | 8/1971 | Klimboff | 117/25 |
| 3,884,706 | 5/1975 | Little | 106/15 |
| 3,888,176 | 6/1975 | Horai et al. | 106/15 |
| 3,888,682 | 6/1975 | Nelson | 106/15 |
| 3,888,683 | 6/1975 | Horai et al. | 106/15 |
| 3,888,684 | 6/1975 | Little | 106/15 |
| 3,894,877 | * 7/1975 | Nelson | 106/18 |
| 3,998,644 | 12/1976 | Lodge | 106/15 |
| 4,092,441 | 5/1978 | Meyer et al. | 427/37 |
| 5,356,664 | 10/1994 | Narayan et al. | 427/186 |
| 5,382,475 | 1/1995 | Kayser | 428/403 |
| 5,411,803 | 5/1995 | George et al. | 428/403 |
| 5,573,782 | * 11/1996 | Bigham et al. | 428/489 |

* cited by examiner

*Primary Examiner*—Anthony Green
(74) *Attorney, Agent, or Firm*—Imre Balogh; William J. Davis (57) ABSTRACT

Algae-resistant roofing granules coated with: a first coat consisting of a fired silicate-clay matrix containing cuprous oxide and zinc sulfide to provide a slow, long-term bimetallic copper and zinc ions release; and a second coat consisting of a fired silicate-clay matrix containing a pigment.

11 Claims, 8 Drawing Sheets

ALGAE-RESISTANT ROOFING GRANULES

BACKGROUND OF THE INVENTION

1. Field of the Invention

The present invention relates to algae-resistant roofing granules. More particularly, it relates to algae-resistant roofing granules of the type which are artificially colored and contain a slow-release bimetallic algicide as a component of the color coating.

2. Reported Development

Roofing granules, both natural and artificially colored granules, are extensively used in roll roofing and asphalt shingle compositions. The roofing granules are embedded in the asphalt coating on the surface of the asphalt-impregnated felt base material, the granules thus forming a coating that provides an adherent, weather-resistant exterior roofing surface.

In warm and humid climates discoloration of asphalt roofing compositions by the growth of algae is of particular concern. To prevent such discoloration the prior art proposed the use of metallic algicides incorporated into roofing granules that are effective in retarding the biological growth of algae. Illustrative examples of prior art compositions are as follows.

U.S. Pat. No. 3,494,727 discloses a microbe resistant roof wherein the roofing material contains embedded therein visually observable metallic chips, such as copper, lead, zinc and iron.

U.S. Pat. No. 3,507,676 discloses zinc-containing coating for roofing granules in the form of zinc, ZnO or ZnS.

U.S. Pat. No. 3,528,842 discloses copper compound-containing algicidal surfacing, the copper compound being cuprous oxide or cuprous bromide.

U.S. Pat. No. 3,598,627 discloses fungus-resistant shingles the outside surface of which are asphalt coated and are covered by a hard, granular weathering material and granular zinc.

U.S. Pat. No. 3,884,706 discloses algicidal roofing granules coated with a substantially water insoluble silicate-clay coating into which small amounts of algicides, e.g. 0.05% to 0.5% zinc algicide and 0.05% to 0.5% copper algicide, are incorporated based on the total weight of the roofing granules.

U.S. Pat. No. 4,092,441 discloses roofing granule treatment by coating the granules with a metallic algicide, such as zinc, copper, nickel and mixtures thereof. The metals are sprayed onto the granules in the form of molten droplets.

U.S. Pat. No. 5,382,475 discloses algicidal granules having a ceramic coating thereon comprising three layers, the first two of which have a copper compound, and the third layer has a pigment, a borate compound and zinc oxide.

While the teaching of the above-mentioned references greatly advanced the state of the art and provided impetus for the building materials industry in creating algicidal roofing granules, the need for creating enhanced, long-term and slow-release algicide-containing granules still exists. The object of the present invention is to provide for that need.

The present invention provides bimetallic algicide-coated granules in which the two metals act synergistically in preventing/retarding the growth of algae.

SUMMARY OF THE INVENTION

The present invention provides algae-retardant, artificially colored roofing granules comprising:

a) a base of crushed mineral aggregates coated with b) a first or inner layer of semi-ceramic composition consisting of a fired silicate-clay matrix containing: of from about 80 pounds to about 180 pounds, and preferably 90 pounds to 115 pounds, cuprous oxide ($Cu_2O$) per ton of the base material; and of from about 6 pounds to about 60 pounds, and preferably 12 pounds to 25 pounds, of zinc sulfide (ZnS) per ton of the base material;

c) a second or outer layer of semi-ceramic composition, coated on the first or inner layer of the semi-ceramic composition, consisting of a fired silicate-clay matrix containing coloring pigments that determine the overall appearance of the granules.

The combination of cuprous oxide and zinc sulfide is a concentrated source of slow-release bimetallic ions, i.e. copper and zinc, that provides a synergistic combination of toxic metal ions for more effective long-term algicidal performance. Unlike cuprous oxide and zinc oxide bimetallic combinations suggested by the prior art wherein the zinc oxide retards the rate of copper ion release, the cuprous oxide and zinc sulfide combination provides a higher rate of copper and zinc ion release. The rate of copper ion release from the cuprous oxide/zinc sulfide combination is proportional to, and can be regulated by, the amount of zinc sulfide present.

Optionally the second or outer layer may contain zinc sulfide, which can function as both a light-colored pigment and a source of slow release zinc algicide. If used in the second or outer layer, the zinc sulfide should be present in an amount of from about 5 pounds to about 30 pounds, and preferably 10 pounds to 20 pounds, per ton of the base material.

The algae-retardant granules of the present invention may be mixed with standard, non-algicidal roofing granules in a ratio of from about 5% w/w to about 60% w/w or higher and preferably from 10% to 20%. The ratio of algae-resistant and non-algae resistant granules can be tailor-made to the geographic area where algae infestation is influenced by the environment. In addition, the desire or requirement of providing a light-colored appearance of the roofing granules will influence the ratio of algicidal and non-algicidal granules in the mixture providing the final product.

The present invention is also directed to the manufacturing of the algae-retardant, artificially colored roofing granules comprising the steps of:

a) crushing and sizing the base aggregate to the desired size, typically to No. 11 grading;

b) pre-heating the sized/graded granules to about 210° F.–230° F.;

c) coating the pre-heated granules with a first or inner coat of ceramic composition being in the from of an aqueous slurry comprising:
Sodium silicate,
Kaolin clay,
Pigment,
Cuprous oxide, and
Zinc sulfide;

d) pre-drying the first or inner coat granules to adjust their moisture content to from about 0.2% to about 0.5% w/w;

e) kiln-firing the granules at a temperature of from about 740° F. to about 760° F. to form an insolubilized silicate-clay matrix coating in which the cuprous oxide, zinc sulfide and pigment are uniformly distributed;

f) cooling the kiln-fired, first-coated granules to a temperature of from about 210° F. to about 230° F.;

g) coating the first or inner coated granules with a second or outer coat of a semi-ceramic aqueous composition comprising:
   Sodium silicate,
   Kaolin clay and
   Pigment;
h) pre-drying the second-coated granules to adjust the moisture content to about 0.2% to 0.5% w/w;
i) kiln-firing the granules at a temperature of from about 890° F. to about 960° F. to form an insolubilized silicate-clay matrix coating in which the pigment is uniformly distributed;
j) reducing the temperature of the granules to about 200° F.–220° F.; and
k) treating the granules with a mixture of process oil and an organosilicone compound to impart dust control and adhesion to a substrate, such as asphalt.

BRIEF DESCRIPTION OF THE DRAWINGS

In the drawings where used, the abbreviations denote the following:
A-902=standard light colored 3-coat product;
PPT=pounds per ton;
PPT/WK=pounds per ton per week; and
AR=algae-retardant.

DETAILED DESCRIPTION OF THE INVENTION

Mineral-surfaced asphalt shingle roofing can support the growth of discoloring algae, most commonly the blue-green type, Cyanobacteria. Such roofs can develop spots of algae colonies within two to three years of exposure, particularly in the southeastern Gulf States, as a result of inoculation by air-born algae spores. These spots gradually grow into unsightly streaks as rain washes spores down the roof. In severe cases with the passage of time, this discoloration will eventually overtake the entire roof.

In addition to being unsightly, algae discoloration reduces the reflectivity of light-colored asphalt shingles and thus increases their peak daytime temperatures. This discoloration can also reduce the effective service life of the roof. Although algae discoloration can be removed by cleaning, the process of removal is costly and has to be repeated every few years. Repeated cleaning also tends to damage the surface of the mineral-surfaced asphalt shingles. A more effective and economical approach is to utilize algae-retardant roofing granules as a component of the asphalt shingles to prevent the growth of discoloring algae. The present invention addresses the problem of discoloration of mineral-surfaced asphalt shingles by algae.

Algae-retardant roofing granules of the present invention are artificially colored mineral aggregate containing a slow-release bimetallic algicide as a component of the color coating. The granules contain a sufficient amount of algicide to allow blending with standard granules having no algicides for long-term protection of the resulting blend. The invention represents an advance in the art by incorporating a unique bimetallic algicide which provides: a higher rate of toxic metal ion release; and a combination of metal ions of synergistic toxicity. This is accomplished by a 2-coat roofing granule manufacturing process, which is significantly cheaper than the 3-coat products previously described.

Roofing Shingles

Roofing shingles typically comprise materials, such as felt and fiberglass to which asphalt is applied to permeate the felt or fiberglass. Over the impregnated felt or fiberglass mineral granules are applied completing the conventional roofing shingles. The granules are obtained from natural base rocks such as greenstone, rhyolite, andesite, basalt, nephaline syanite, and the like.

The Process for Preparing the Algicidal Granules

The essential steps in the manufacturing process of the roofing granules are as follows.

1. Crushing and sizing the base mineral aggregates to the desired size, typically to No. 11, grading and pre-heating the granules to about 210° F. to 230° F.
2. Coating the preheated granules with a first coat of a semi-ceramic composition, typically comprising the following expressed in pounds per ton, of base mineral aggregate, hereinafter sometimes referred to as PPT (corresponding approximately to gram per 2 kilogram):

| | |
|---|---|
| Water | 40 |
| Sodium silicate solution (38% solids, $SiO_2/Na_2O$ = 2.9) | 75 |
| Kaolin clay | 35 |
| Pigments | 0–10 |
| Cuprous oxide | 90–125 and |
| Zinc Sulfide | 12–25. |

These components are combined into a slurry by using a suitable mixing equipment. The slurry is then applied to the preheated granules in a suitable apparatus to produce the first-coated granules.

3. Predrying the first-coated granules by adjusting the temperature and air flow in the apparatus to reduce their moisture content to about 0.2% to 0.5%.
4. Kiln-firing the predried granules at a temperature of from about 740° F. to about 760° F. to form an insolubilized silicate-clay matrix coating on the granules in which the cuprous oxide, zinc sulfide, and pigments are uniformly distributed.
5. Cooling the fired first-coated granules to a temperature of from about 210° F. to about 230° F. by means of air flow and/or water application in a suitable apparatus.
6. Coating the cooled first-coated granules with a second coat of semi-ceramic composition of which the following is typical expressed in PPT:

| | |
|---|---|
| Water | 25 |
| Sodium silicate solution (40% solids, $SiO_2Na_2O$ = 2.5) | 56 |
| Kaolin Clay | 25 |
| Pigments | 0–15. |

These components are also combined into a slurry using a suitable mixing equipment. The slurry is then applied to the first-coated cooled granules in a suitable apparatus to produce the second-coated granules.

Pigments, when used in the first or second coating may be pigments that are commercially available including: carbon black, titanium dioxide, chromium oxide, yellow iron oxide, ultramarine blue, red iron oxide, metal ferrites, and mixtures thereof. A preferred pigment is zinc sulfide in the second coating which can function as both a light-colored pigment and as a source of slow release zinc algicide.

7. Predrying the second-coated granules by adjusting the temperature and airflow to reduce their moisture content to about 0.2% to 0.5%.
8. Kiln firing the predried second-coated granules at a temperature of from about 890° to about 910° F. to form an insolubilized silicate-clay matrix coating in which the pigments are uniformly distributed.
9. Cooling the kiln-fired second-coated granules by means of air flow and/or water application in a suitable apparatus to reduce their temperature to about 200° to 220° F.
10. Treating the color-coated algae retardant granules with a mixture of process oil and an organosilicone compound well known in the art to impart dust control and to improve asphalt adhesion.
11. Applying the granules to the asphalt coated roof shingles using conventional techniques.

Performance Evaluation

A) Measurement of Copper/zinc Leach Rates

Laboratory soxhlet leaching studies quantified the rates of copper and zinc release from the algae resistant granules produced in pilot plant operation. The data and graphs shown in the Figures and Graphs illustrate the benefits of zinc sulfide over other zinc compounds when used in combination with cuprous oxide.

Figure 1A:
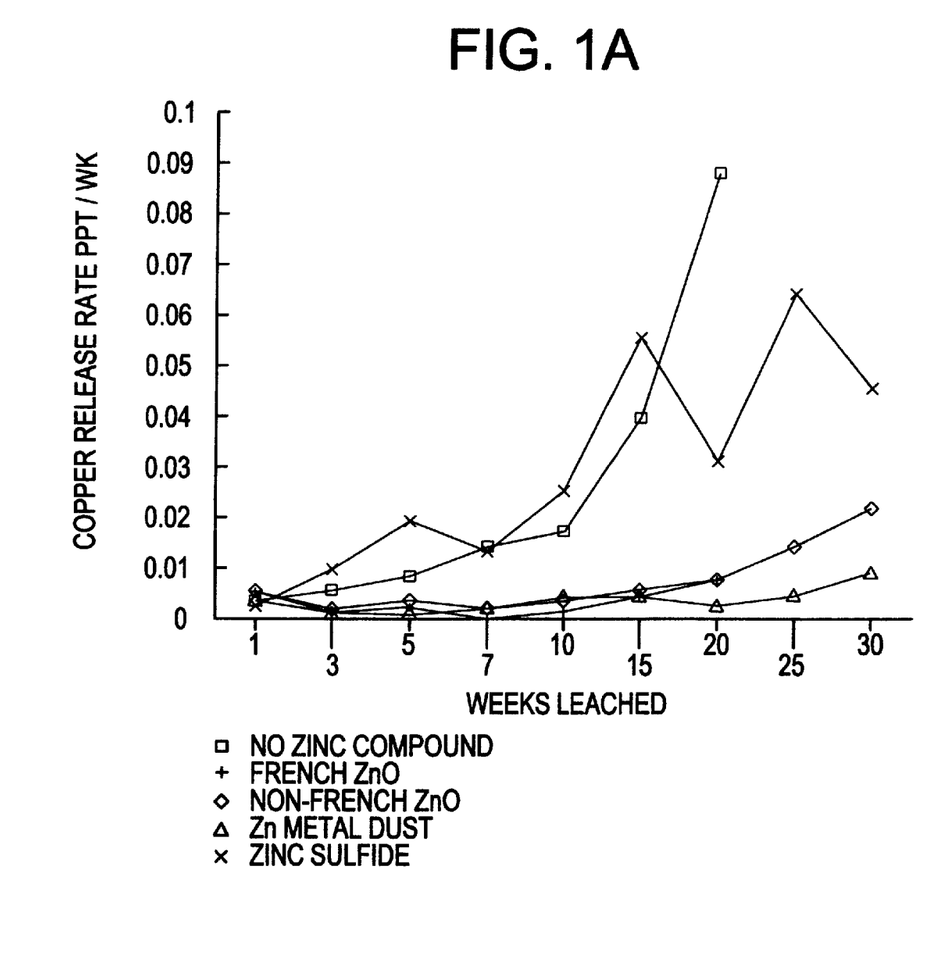
FIG. 1A shows the effect of zinc on A-902 copper release.

FIG. 1A shows the effect of zinc on A-902 copper release, i.e. the effect of a 60 PPT zinc compound loading on A-902 copper/zinc release characteristics. The A-902 product contains 80 PPT cuprous oxide distributed among the $1^{st}$, $2^{nd}$, and $3^{rd}$ coat as 40/40/0 PPT. When present, the 60 PPT zinc compounds are distributed as 25/25/10 PPT. In the Fig. copper release rates are seen to be significantly retarded in the presence of either the French process ZnO, non-French process ZnO, or zinc metal dust. In contrast, zinc sulfide has little effect on the rate of copper ion release.

As used herein, zinc oxide made by the French process differs from the zinc oxide manufactured by the non-French or American process. The difference is discussed is Encyclopedia of chemical Technology, Vol. 24, $3^{rd}$ Ed. John Wiley & Sons, New York, pp. 854–863.

Figure 1B:
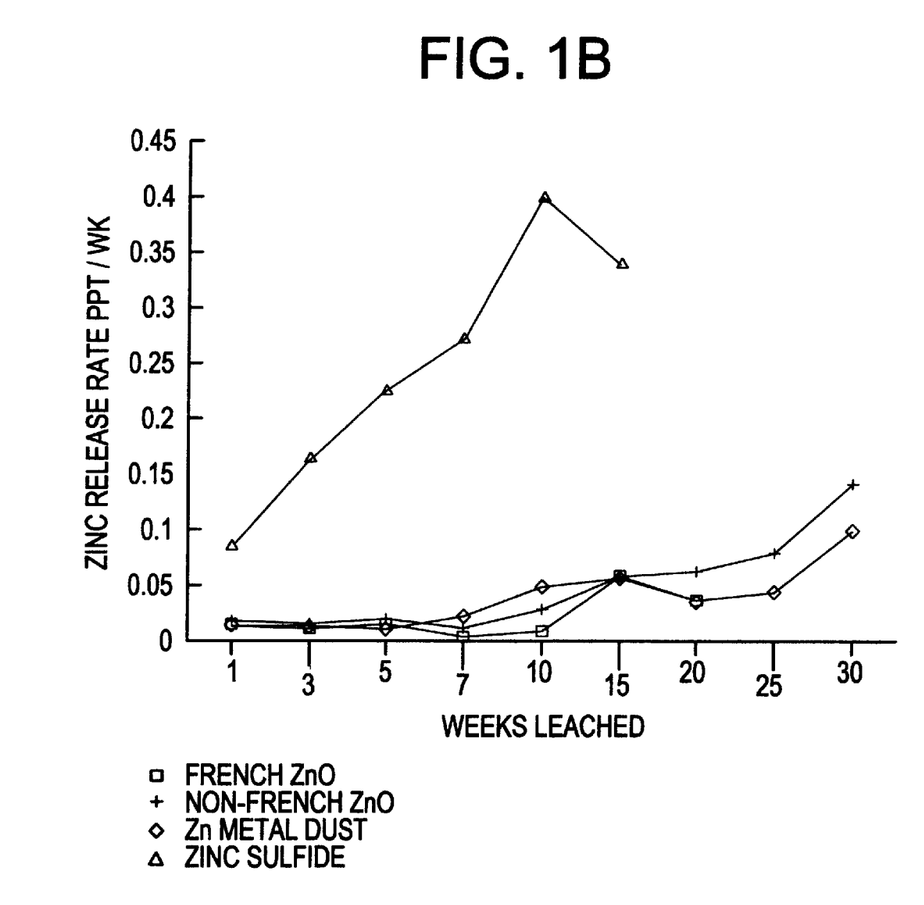
FIG. 1B shows the effect of zinc on A-902 zinc release.

In FIG. 1B, zinc sulfide provides the highest rate of zinc ion release.

Figure 2A:
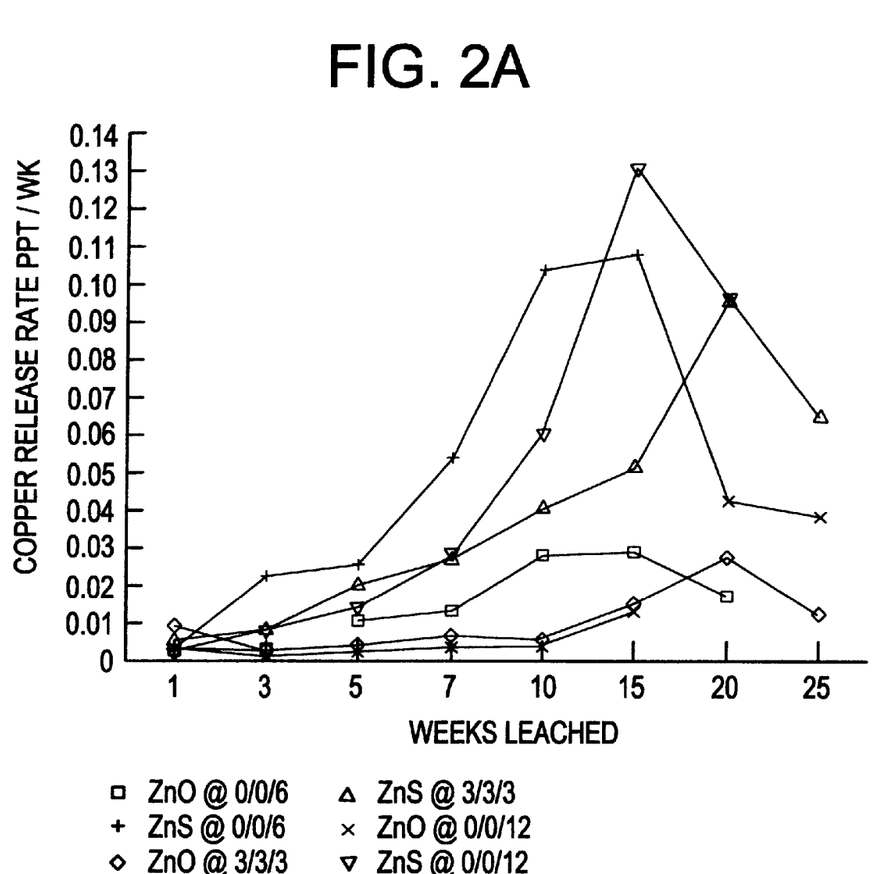
FIG. 2A shows the effect of zinc on A-902 copper release.
Figure 2B:
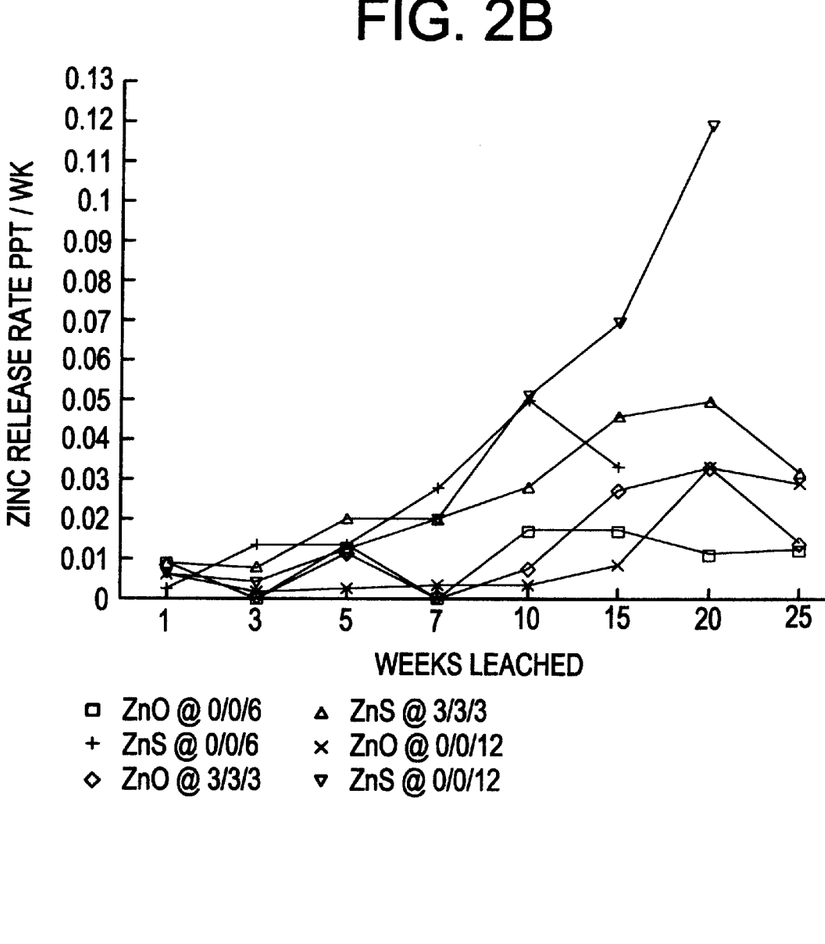
FIG. 2B shows the effect of zinc on A-902 zinc release.

FIGS. 2A and 2B show the effect of 6, 9 and 12 PPT zinc oxide/zinc sulfide loadings on A-902 copper/zinc release characteristics. In this case, the 3-coat A-902 product again contains 80 PPT cuprous oxide distributed as in FIGS. 1A and 1B. However, the zinc oxide and zinc sulfide are distributed (PPT) as 0/0/6, 3/3/3, and 0/0/12. The Figs. show that at these loadings zinc sulfide is again superior to zinc oxide in that zinc sulfide has much less effect on A-902 copper release rates and provides a higher release of zinc ions.

Figure 3:
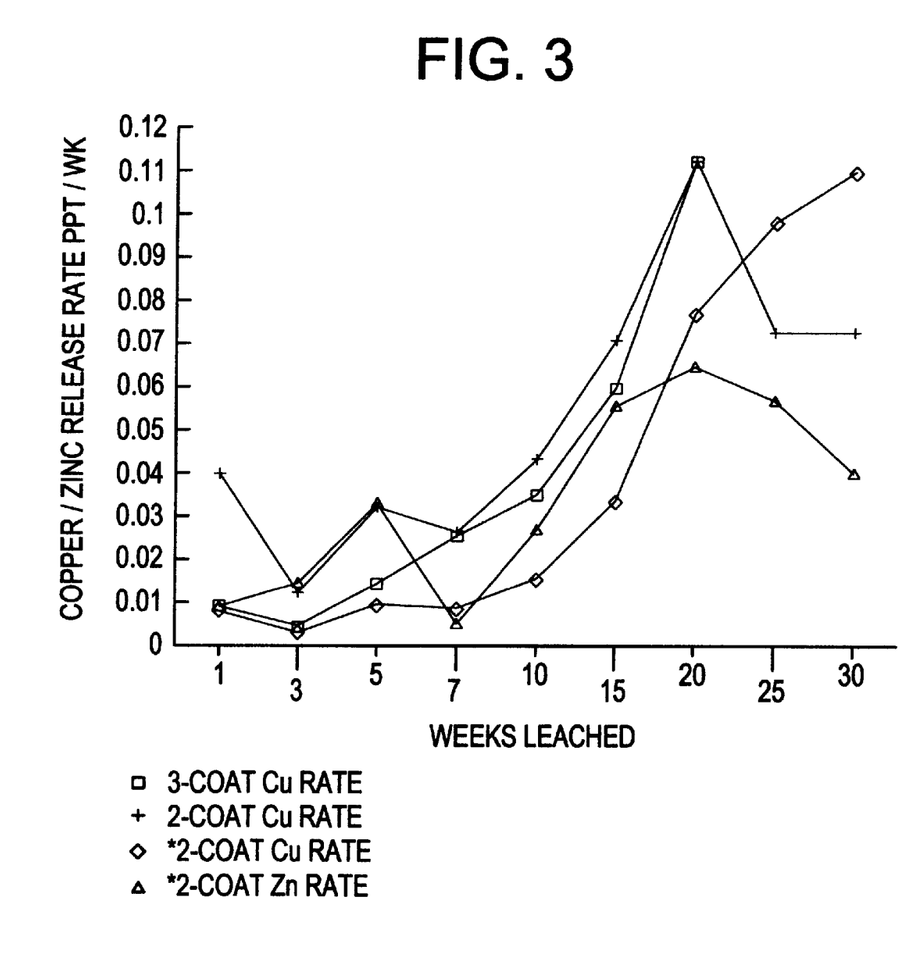
FIG. 3 shows 2-coat A-902 copper/zinc leach rates.

FIG. 3 compares the rates of copper and zinc release characteristics for the improved 2-coat algae retardant products with those of the previously described, standard 3-coat products. In this case, the 3-coat product again contains 80 PPT cuprous oxide distributed as before, namely 40/40/0.

However, the 2-coat product contains 105 PPT cuprous oxide distributed as 105/0. The 2-coat product is seen in FIG. 3 to exhibit a copper release rate comparable to that of the 3-coat products. With the addition of zinc sulfide (12/0) to the 105/0 cuprous oxide, the enhanced 2-coat product shows a copper release rate that is unaffected in magnitude, but is shifted to a slightly longer development time. In addition to the copper, the enhanced 2-coat product provides a significant level of zinc ion release.

B) Liquid Algae Culture Studies

The toxicity of various levels of copper and zinc ions toward Gloeocapsa Alpicola was determined in liquid culture studies. Nutrient solutions containing fixed concentrations of copper, zinc and copper plus zinc combinations (from sulfate salts) were inoculated with Gloeocapsa Alpicola and the rate of growth measured by spectrophotometric chlorophyll analysis over several days.

Figure 4A:
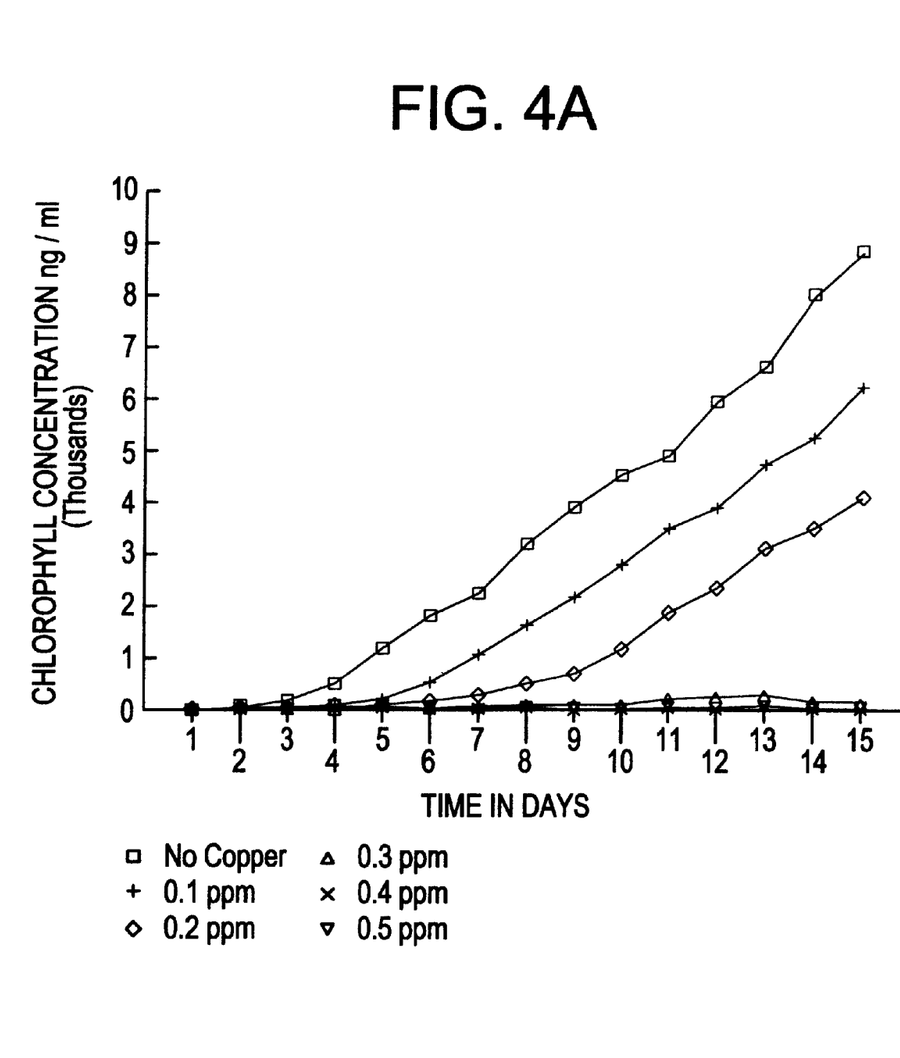
FIG. 4A shows Gloeocapsa Alpicola growth rates at various copper concentrations.

FIG. 4A shows that the threshold copper concentration required to inhibit the growth of Gloeocapsa Alpicola is about 0.3 ppm.

Figure 4B:
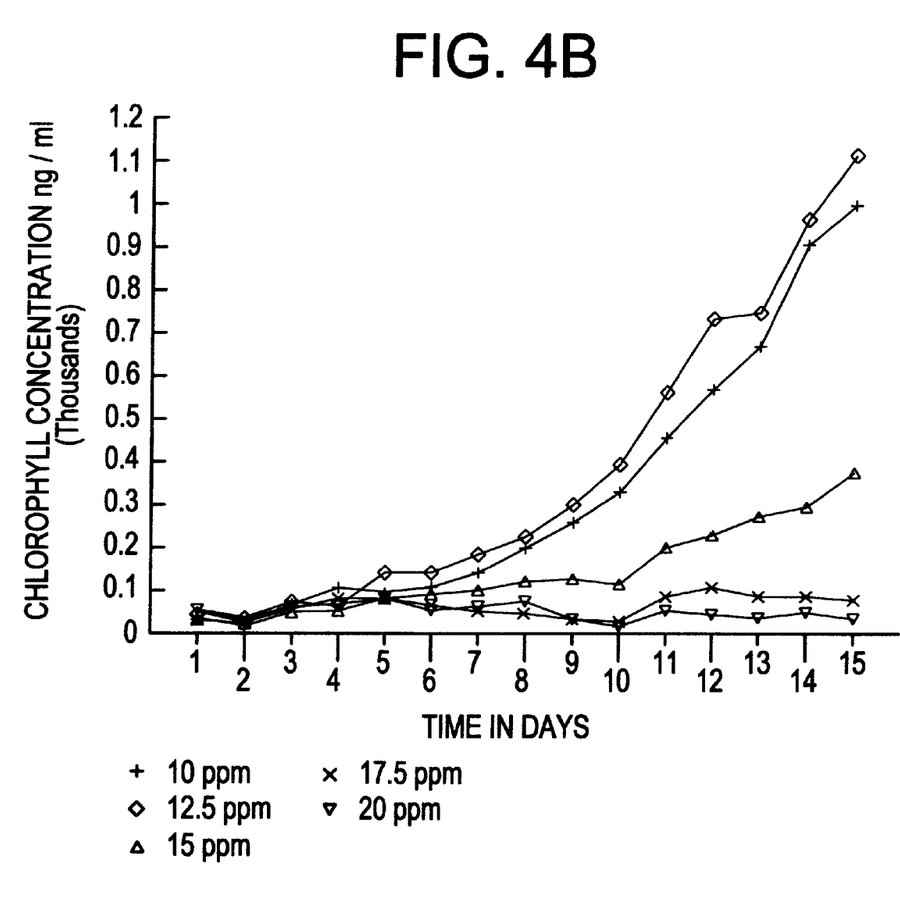
FIG. 4B shows Gloeocapsa Alpicola growth rates at various zinc concentrations.

FIG. 4B shows that the threshold zinc concentration required to inhibit the growth of Gloeoxapsa Alpicola is about 18 ppm.

Figure 4C:
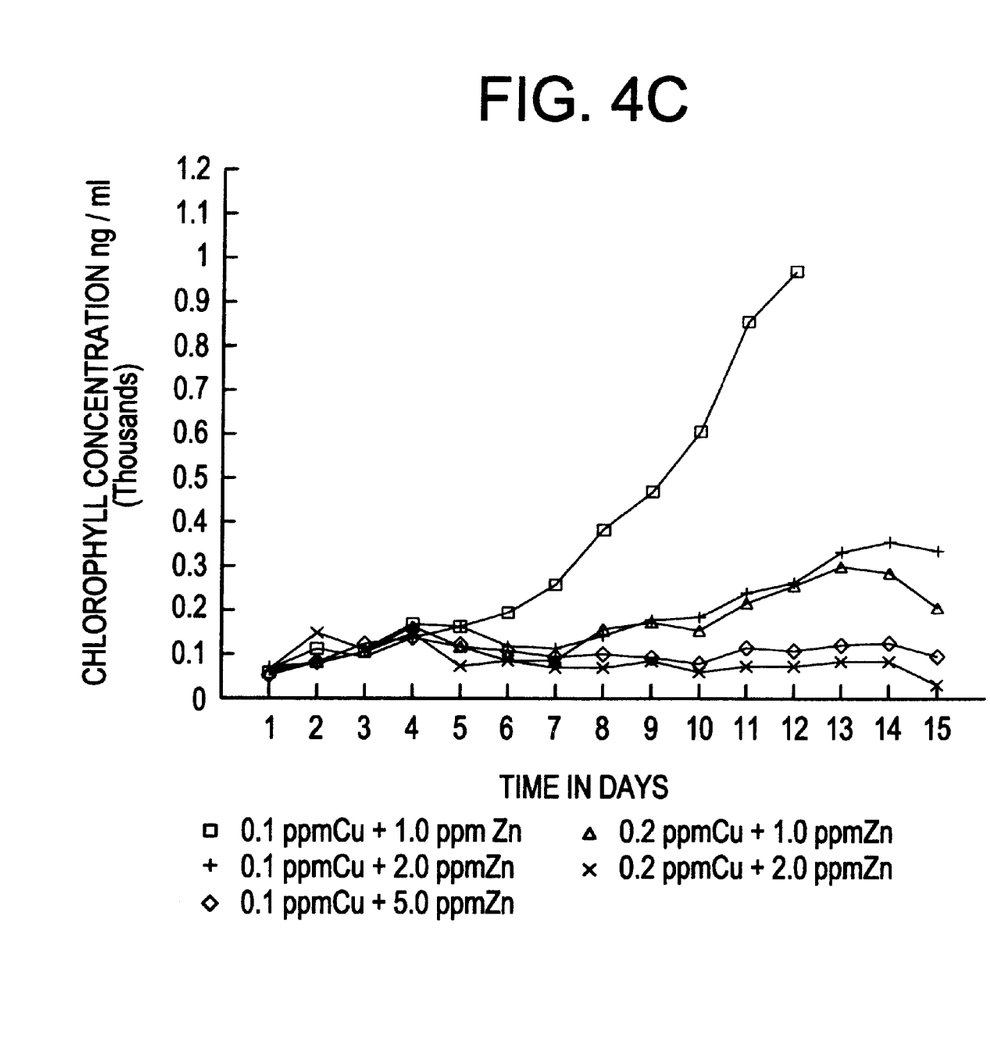
FIG. 4C shows Gloeocapsa Alpicola growth rates at synergistic [Cu++]+[Zn++] combinations.

FIG. 4C shows that a combination of copper and zinc is more effective than either the copper or zinc alone, i.e. the combination exhibits synergistic toxicity. Gloeocapsa Alpicola growth inhibition is achieved with only 0.1 ppm copper and 5 ppm zinc, or with 0.2 ppm copper and 2 ppm zinc.

Various modifications of the present invention will become apparent to those skilled in the art without departing from the spirit and scope of the invention as defined in the appendent claims.

What is claimed is:

1. Algae-retardant roofing granules having an enhanced ability, over an extended period of time, to release bimetallic algicidal ions to prevent or inhibit the growth of algae and fungi upon atmospheric exposure of roofing surfaces coated with such granules comprising:
   a) a base material of crushed mineral aggregates in the form of granules coated with:
   b) a first layer of semi-ceramic composition consisting of a fired silicate-clay matrix containing from about 80 pounds to about 180 pounds of cuprous oxide per ton of said base material, and from about 6 pounds to about 60 pounds of zinc sulfide per ton of said base material; and
   c) a second layer of semi-ceramic composition consisting of a fired silicate-clay matrix containing: about 22.4 pounds of sodium silicate per ton of said base material; about 25 pounds of Kaolin clay per ton of said base material; and about 0–15 pounds of a pigment per ton of said base material.

2. The algae-retardant roofing granules of claim 1 wherein said second layer of semi-ceramic composition further comprises from about 5 pounds to about 30 pounds of zinc sulfide per ton of said base material.

3. The algae-retardant roofing granules of claim 2 wherein said second layer of semi-ceramic composition further comprises from about 10 pounds to about 20 pounds of zinc sulfide per ton of said base material.

4. The algae-retardant roofing granules of claim 1 wherein said first layer of semi-ceramic composition contains from about 90 pounds to about 115 pounds of cuprous oxide per ton of said base material.

5. The algae-retardant roofing granules of claim 1 admixed with non-algae-retardant roofing granules in a ratio of 5% to 60% algae retardant granules to 95% to 40% non-algae retardant roofing granules.

6. The algae-retardant roofing granules of claim 1 wherein said pigment is present from zero to 10 pounds per ton of said base material.

7. The algae-retardant roofing granules of claim 1 wherein said pigment is selected from the group consisting of: zinc sulfide, carbon black, titanium dioxide, chromium oxide, yellow iron oxide, ultramarine blue, red iron oxides and metal ferrites.

8. The algae-retardant roofing granules of claim 7 wherein said zinc sulfide functions as an algae retardant and as a coloring pigment.

9. A method of preparing algae-retardant, artificially colored roofing granules comprising the steps of:
   a) crushing and sizing a base mineral aggregate to form granules therefrom;
   b) preheating the granules to about 210° F.–230° F.;
   c) coating the preheated granules with a first coat of semi-ceramic composition of an aqueous slurry comprising:
      about 75 pounds of 38% solids sodium silicate solution per ton of said base mineral aggregate,
      about 35 pounds Kaolin clay per ton of said base mineral aggregate,
      about 90–125 pounds cuprous oxide per ton of said base mineral aggregate, and
      about 12–25 pounds zinc sulfide per ton of said base mineral aggregate;
   d) predrying the first-coated granules to a moisture content of about 0.2% to 0.5%;
   e) kiln-firing the predried granules at a temperature of from about 740° F. to 760° F. to form an insolubilized silicate-clay matrix coating;
   f) cooling the kiln-fired, first coated granules to a temperature of from about 210° F. to about 230° F.;
   g) coating the cooled granules with a second coat of a semi-ceramic composition of an aqueous slurry comprising:
      about 40 pounds sodium silicate per ton of said base mineral aggregate,
      about 25 pounds Kaolin clay per ton of said base mineral aggregate, and
      about 0–15 pounds pigment per ton of said base mineral aggregate;
   h) pre-drying the second coated granules to a moisture content of about 0.2% to 0.5%;
   i) kiln-firing the granules at a temperature of from about 890° F. to about 910° F. to form an insolubilized silicate-clay matrix coating;
   j) reducing the temperature of the granules to about 200° F. to 220° F.; and
   k) treating the granules with a mixture of a process oil and an organosilicone compound to impart dust control and adhesion to a substrate.

10. The method of claim 9 wherein said pigment is selected from the group consisting of:
   zinc sulfide, carbon black, titanium dioxide, chromium oxide, yellow iron oxide, ultramarine blue, red ion oxides and metal ferrites.

11. A method of protecting asphalt-coated roof shingles against algae and fungi comprising the steps of:
   (a) providing asphalt-coated roof shingles;
   (b) providing a base mineral aggregate and forming granules therefrom;
   (c) coating said granules with a first layer of a semi-ceramic composition consisting of a fired silicate-clay matrix containing from about 80 pounds to about 180 pounds of cuprous oxide per ton of said granules, and from about 6 pounds to about 60 pounds of zinc sulfide per ton of said granules to obtain a first layer coated granules;
   (d) coating said first layer coated granules with a second layer of a semi-ceramic composition consisting of a fired silicate-clay matrix containing: about 40 pounds of sodium silicate per ton of said granules; about 25 pounds of Kaolin clay per ton of said granules; and about 0 to 15 pounds of a pigment per ton of said granules to obtain a second layer coated granules;
   (e) treating said first and said second layer coated granules with a mixture of a process oil and an organosilicone compound to impart dust control and adhesive properties thereto to obtain treated granules ready for coating said asphalt coated roof shingles; and
   (f) applying said treated granules to said roof shingles to obtain algae and fungi-resistant roof shingles,
wherein said cuprous oxide and zinc sulfide release toxic copper and zinc ions for an effective inhibition of algae and fungi.

* * * * *